United States Patent [19]

Hwang et al.

[11] Patent Number: 4,985,439
[45] Date of Patent: Jan. 15, 1991

[54] GLUCOSE TOLERANCE FACTOR AND METHOD OF MAKING SAME

[75] Inventors: David Hwang, Arcadia; Arye Lev-Ran, Cypress; Ken Barseghian, deceased, late of Glendale, all of Calif., by Iemma Barseghian, legal representative

[73] Assignee: Anheuser-Busch Companies, Inc., St. Louis, Mo.

[21] Appl. No.: 480,369

[22] Filed: Feb. 14, 1990

Related U.S. Application Data

[63] Continuation of Ser. No. 104,084, filed as PCT US 86/02493, Nov. 19, 1987, published as WO87/03200 on Jun. 4, 1987, abandoned, which is a continuation-in-part of Ser. No. 795,977, Nov. 21, 1985, abandoned.

[51] Int. Cl.$^5$ .............................................. A61K 31/47
[52] U.S. Cl. .................................... 514/312; 514/313; 514/866; 514/884
[58] Field of Search ................. 435/68, 256, 941, 942; 514/2, 312, 313, 866, 884; 424/103, 195.1

[56] References Cited

U.S. PATENT DOCUMENTS 4,242,257 12/1980 Silio ........................... 260/112.5 R
4,343,905 8/1982 Szalay ................................ 435/256

OTHER PUBLICATIONS

Wojahn, *Arznceimittel Forsch.*, 2:163–165 (1952).
Toepfer, E. W. et al., *J. Agric. Food Chem.*, 25: 162–166 (1977).
Davies, D. M. et al., *Biomed. Med.*, 33: 297–311 (1985).
Barrett, J. et al., *Polyhedron*, 4: 1–14 (1985).
Mirsky, N. et al., *J. Inorg. Biochem.*, 13: 11–21 (1980).
Holdsworth, E. S. et al., *J. Inorganic Biochem.*, 21: 31–44 (1984).
Kumpulainen, J. et al., *Bioinorganic Chemistry*, 8: 419–429 (1978).
Haylock, S. J. et al., *J. Inorganic Biochemistry*, 18: 195–211 (1983).
Mertz, W., *Nutrition Reviews*, 33: 129–135 (1975).
Haylock, S. J. et al., *J. Inorganic Biochemistry*, 19: 105–107 (1983).
Tuman, R. W. et al., *Diabetes*, 26: 820–825 (1977).

*Primary Examiner*—John W. Rollins
*Attorney, Agent, or Firm*—Sterne, Kessler, Goldstein & Fox

[57] ABSTRACT

A glucose tolerance factor which reduces blood sugar in mammals and is derived from yeast. The glucose tolerance factor can be isolated from autolyzed brewer's yeast extract by sequential fractionation on Sephadex G-75, Biogel P-6, Biogel P-2, to give a purified glucose tolerance factor. By further purification, a substantially purified glucose tolerance factor is obtained which is a quinoline derivative with a molecular ion at 174 by mass spectrometry.

3 Claims, No Drawings

GLUCOSE TOLERANCE FACTOR AND METHOD OF MAKING SAME

CROSS-REFERENCE TO RELATED APPLICATIONS

This application is a continuation of application Ser. No. 7/104,084, filed as PCT US 86/02493 on Nov. 19, 1987, published as WO87/03200 on Jun. 4, 1987 now abandoned, which is a continuation-in-part of U.S. application Ser. No. 795,977, filed Nov. 21, 1985, all sujbect matter of which is incorporated by reference.

TECHNICAL FIELD

This invention relates to glucose tolerance factor (GTF) and specifically to a glucose tolerance factor isolated from yeast which is useful in lowering blood sugar in mammals and to a quinoline derivative contained in the GTF fraction. The invention relates as well to a process for isolating GTF in substantially pure form.

BACKGROUND ART

In an article entitled "High-Chromium Yeast and Glucose Tolerance Factor", McCarthy et al., *J. Prevention Medicine*, Vol. 2 (1983), McCarthy discussed the history of glucose tolerance factor and its discovery in the 1950's by Schwarz and Mertz. GTF was found to be associated with trivalent chromium.

Brewer's yeast was found to be an effective source of GTF with chromium. Torula yeast is low in chromium; chromium-deficient rats fed a diet of torula yeast continued to demonstrate impaired glucose tolerance.

In almost all subsequent work, attention was concentrated on the isolation and characterization of the chromium-containing fractions from brewer's yeast or other sources and on the evaluation of the chromium status of man and metabolic effects of chromium or GTF-enriched diets.

In Szalay, U.S. Pat. No. 4,343,905, the patentee attempted to concentrate GTF-chromium complex from synthetically processed brewer's yeast by reacting it with chromium oxide and amino acids. Szalay stated that the presence of chromium as an inorganic salt in food produces an increase in glucose oxidation in a human's biological system, particularly when extracts of brewer's yeast containing chromium are added.

The relationship of chromium content in food and its effects on glucose oxidation activity are discussed, for example, in Toepfer et al., "Chromium Foods in Relation to Biological Activity," *J. Agr. Food Chem.* 21:69 (1973). Specifically, this article described the biological activity of various chromium-containing foods and the relationship of GTF activity (expressed as a function of increased insulin response with chromium) to chromium content.

Other workers have concurred in the existence of chromium-containing GTF based on other observations. Chromium salts in the concentration 1 ppm increased cell carbon dioxide production after a lag period of 3 hours while chromium-containing yeast fractions stimulated the process immediately. In chromium-deficient rats, mice, and squirrel monkeys, impaired glucose tolerance could be improved overnight by both chromium salts and yeast extracts, but the latter was more efficient and acted more quickly. In humans, chromium improved glucose tolerance in certain undernourished children and in one patient who became chromium deficient while receiving total parenteral nutrition. Jeejeebhoy, *Am. J. Clin. Nutr* 30:531–538 (1977). Intestinal absorption of chromium was much more effective from GTF than from inorganic salts. In vitro GTF increased insulin effects on glucose uptake and glucose carbon incorporation in rat epididymal fat pad (the fat pad assay) and on the incorporation of certain amino acids into proteins. Chromium salts were also effective, but only in higher concentration.

Puzzling was the fact that glucose intolerance in chromium-deficient animals could be corrected as quickly with chromium as with GTF. This observation made it unlikely that chromium, in order to be effective, had to be incorporated into GTF in vivo. At the same time, one observation seemed to be crucial as a proof of the biological role of GTF: although certain tissues of fetuses contain significant amounts of chromium, inorganic chromium does not cross the placenta while GTF does. Mertz, *Nutrition Rev.* 33:129–135 (1975).

Additional proof was provided by experience with genetically diabetic db/db mice. Whereas inorganic chromium was without effect, GTF from brewer's yeast or from pork kidneys, when given intraperitoneally, significantly decreased plasma glucose (but did not normalize it). Its effect was most pronounced in those animals that displayed both hyperglycemia and hyperinsulinemia. The authors concluded that such animals probably did not synthesize GTF and that GTF potentiated the effect of endogenous insulin, thus abolishing or diminishing insulin resistance. Tuman et al., *Diabetes* 26:820–826 (1977).

In elderly people, Chromium supplementation resulted in some improvement of carbohydrate tolerance. Potter et al., *Metabolism* 34:199–204 (1985); Martinez et al. *Nutr. Research* 5:609–620 (1985). Even more effective was high-Chromium yeast. These results were not confirmed in well-fed elderly people. Offenbacher et al., *Am. J. Clin. Nutr.* 42:454–461 (1985).

Brewer's yeast (but not chromium-poor torula yeast) improved glucose tolerance and after glucose load in elderly humans (Offenbacher et al., *Diabetes* 29:919–925 (1980)), but not in diabetics (Rabinowitz, *Diabetes Care* 6:319–327 (1983)). Similarly, inorganic chromium slightly decreased fasting and postprandial plasma glucose in persons age 21–69 in whom 90-minute post-load plasma glucose was about 100 mg/dl (Anderson, *Metabolism* 21:984–899 (1983)). This result was not confirmed in diabetics. Uusitupa, Uusitupa, *Am. J. Clin Nutr.* 38:404–410 (1983); Rabinowitz et al., *Biol. Trace Elem. Research* 5:449–466 (1983).

There have been many unsuccessful attempts both to determine the chemical structure of GTF and to separate out pure GTF from brewer's yeast. In an early method, brewer's yeast was extracted with 50% ethanol, the aqueous phase acidified, absorbed on charcoal, eluted with ammonium hydroxide and purified on cation or anion exchange resins followed by gel filtration. It was found that the presumed GTF contained two molecules of nicotinic acid. Since this left four other coordination sites of chromium unoccupied, it was presumed that these sites were linked to glutamic acid, glycine and a sulfur-containing amino acid, such as cysteine. This combination was presumed to stabilize the complex and preserve its biologic activity. Indeed, freshly synthesized complexes or mixtures of all these substances exerted GTF-like effects in the fat pad assay (Toepfer, *J. Agric. Food Chem.* 25:162–166 (1977)) and on db/db mice. However, these complexes were very unstable, and completely lost their activity within 10 days. In addition, the biological activity was inferior to that of natural GTF. Tuman, *Diabetes* 27:49-56 (1978). It became clear that larger amounts of chromium in yeast did not increase GTF activity. This point was first commented on by Mertz, *Nutrition Rev.* 33:129-135 (1975).

Work from several centers published recently gave a new twist to the GTF problem. One group (Mirsky, *J. Inoroanic Biochem.* 13:11-21, (1980)) isolated a factor by extraction in butanol-water followed by dialysis against water, chromatography on a DEAE cellulose column, and gradient elution, first with water and then with increasing concentrations of ammonium hydroxide. Biological activity was found in the water eluent only.

Further purification was achieved on a Dowex-50x8 column. The resultant GTF increased carbon dioxide production by yeast cells after a lag time of 20-50 minutes. The lag could be abolished by preincubation of the yeast with glucose. The preparation showed increased effectiveness in a chromium content range of 0.3-6 ng/ml.

An interesting finding was that GTF exerted the same effect on fructose, mannose, and lactose. Later it was found that GTF also increased 2-deoxyglucose uptake which suggested that the primary effect of GTF was on sugar transport. It was suggested that the role of GTF in yeast may be similar to the effect of insulin in animals. Mirsky et al., *J. Inoroanic Biochem.* 15:275-279 (1981).

These data, however, were not completely confirmed by others. Holdsworth et al. showed that GTF prepared by an identical method increased decarboxylation of pyruvate to ethanol and carbon dioxide; glucose metabolism was enhanced when cells were preincubated with GTF itself for 30-60 minutes; and that GTF increased the cell utilization of ethanol (which freely permeates the cells). Hoodsworth et al., *J. Inoroanic Biochem.* 21:31-44 (1984). Since GTF, in addition to pyruvate decarboxylase, also stimulated pyruvate carboxylase (which fixes bicarbonate carbon), the question arose whether GTF was indeed one substance. This preparation, presumably one of the purest available, was not reported to have been tested on animal cells or in db/db mice.

Using the same biological model (carbon dioxide production by yeast) another group (Haylock, *J. Inorganic Biochem.* 18:195-211 (1983)) studied both a natural GTF preparation (isolated from the Merck yeast extract) and the synthetic product of Toepfer supra. First, they isolated eleven chromium-containing fractions, but found that the anionic and neutral fractions totally lacked biological activity. Four cationic fractions were found active. The authors also isolated active fractions from molasses, black peppercorns and pork kidneys. Peaks of elution from the ion-exchange column were found between pH's 1.75 to 12, thus showing the heterogeneity of the active components. Even more important, the authors found that most of the absorbance at 262 nm recorded by Toepfer was caused by free nicotinic acid. They concluded that it was not established that the natural GTF-active principle obtained from brewer's yeast is actually a chromium-nicotinic acid-amino acid complex.

Other work from the same laboratory (Haylock et al., *J. Inorganic Biochm.* 19:105-117 (1983)) threw additional light on the problem. It was found that most of the eleven fractions were artifacts which resulted from the direct reaction between chromium and components of the medium. Two biologically active fractions (P3 and P4) were isolated. The most active fraction (P3) was heavily contaminated with salt and was not further purified. The mass spectrum showed some evidence of the presence of tyramine. The P4 fraction consisted of 90% tyramine (which itself was not biologically active) and was considered largely impure. The most important finding was that the biologically active peaks and chromium peaks were clearly distinct. The authors concluded that GTF did not contain chromium. They explained the opposite findings of others by their inability to elute separately cationic components with GTF activity and cationic chromium compounds. The authors stated that chromium complexes from yeast played no role in yeast metabolism and that yeast cells did not convert chromium into a specific biologically active form.

A more recent report discloses the isolation of two chromium-free amino compounds from yeast with GTF activity. Davies et al., *Biochem. Med.* 33:297-311 (1985). The purification involved an initial separation of anionic and cationic fractions on a DEAE cellulose column. The cationic material was fractionated on a Dowex 50W-X8(H+) ion exchange resin using a gradient elution. A second separation of the active fractions was performed on Dowex 50W-X2 formate column. Active material was further purified by gel filtration on Bio-Gel P-4. Preparative paper chromatography was used to isolate a compound with GTF activity which was identified as ornithine by paper chromatography, $^{13}$CNMR and by fast-atom bombardment mass spectrometry.

The anionic material obtained from the DEAE cellulose column was chromatographed on a DEAE sephacrel column using a gradient elution. The active fractions were eluted with HCl and were subjected to mild acid hydrolysis followed by fractionation on a Dowex 50W-X2 column eluted with a triethylamine/ammonia gradient. The active fraction was subjected to preparative paper chromatography to give an active fraction that was tentatively identified as N-glutaryllysine or a similar substituted lysine.

Although the two isolated fractions possess GTF-like activity, the authors have not presented any data to prove that it is actually ornithine and a substituted lysine which is responsible for the GTF activity and not an impurity therein. In addition, the authors have not shown that they have isolated all materials from yeast having GTF activity.

DISCLOSURE OF THE INVENTION

The present invention comprises a novel process of separating a glucose tolerance factor from brewer's yeast which has blood sugar reducing properties when given to mammals. The invention also relates to novel glucose tolerance fractions and to a purified quinoline derivative thereof.

Recognizing the pharmacological potential for GTF as a therapeutic compound in the treatment of a variety of mammalian health problems, the inventors concluded that a need had continued to exist for a process for isolating and characterizing GTF active materials.

BEST MODE(S) OF CARRYING OUT THE INVENTION

By the term glucose tolerance factor (GTF) is intended materials which have blood sugar reducing properties when given to mammals.

The GTF of the present invention is characterized by its method of isolation and purification, as well as its structural and physiochemical characterisitcs. The term includes that product which may be recovered by a process whereby yeast is harvested and lysed, filtered to remove cellular debris and particulate matter, gel filtered on a column capable of retaining materials having a molecular weight of 50,000 or less, eluted from the gel filtration column, further purified by gel filtration on a column which retains molecules having a molecular weight of 6000 or less, and further gel filtered on a column retaining molecules having a molecular weight of 2000 or less, and further purified by reverse phase HPLC. This material may then be substantially purified by another reverse phase fractionation.

In the practice of this invention, GTF may be isolated from sources including, but not limited to, yeast or an autolyzed extract thereof, molasses, black peppercorns, or pork kidneys. In a preferred embodiment, GTF is isolated from an autolyzed brewer's yeast extract or from fresh brewer's yeast. In either event, brewer's yeast is grown in any conventional manner well known to those skilled in the art.

The biological activities of the putative GTF in various fractions may be determined by assays known to those skilled in the art. These methods include, but are not limited to, in vitro measurement of $^{14}$C-glucose uptake, glucose oxidation, and lipid synthesis in rat adipocytes. Also included are in vivo measurements of glucose reduction, enhancement of carbon dioxide production in yeast, and reduction of blood triglyceride and cholesterol levels in animals.

Yeast is harvested and lysed according to methods well known in the art. The GTF-containing material is first treated to remove cellular debris and particulate matter. Separation methods include, but are not limited to, centrifugation and filtration. A preferred method is centrifugation.

The supernatant containing the active GTF fraction is then applied to a gel filtration column capable of retaining materials of molecular weight 50,000 or less and eluted with an appropriate solvent. Suitable gel filtration materials include, but are not limited to, Sephadex G-75 and Biogel P-60. A preferred gel filtration material is Sephadex G-75. A preferred elution solvent is water.

The biological activity of each fraction may be determined by any of the methods defined above. A preferred method is, the in vitro determination of $^{14}$C-glucose uptake and lipid synthesis in rat adipocytes.

The fractions containing active material are then pooled and concentrated by methods known in the art. Such methods include lyophilization.

The biologically active fraction is further purified by the selective precipitation of inactive materials. This may be accomplished by dissolving 60-90 mg of biologically active material in 1-10 ml of water followed by the addition of 1-10 volumes of 95% ethanol and acidification with a acid to give a final concentration of 0.01-1 N acid. Suitable acids include, but are not limited to HCl, HBr, HI H$_2$SO, NaHSO$_4$, H$_3$PO$_4$, NaH$_2$PO$_4$, p-toluenesulfonic acid, acetic acid, and HNO$_3$. A preferred solvent system includes 5 ml H$_2$O, and 12 ml 95% ethanol, acidified to a concentration of 0.15 N HCl.

The precipitate is removed by methods known in the art including, but no limited to, filtration and centrifugation. The soluble GTF is then concentrated by lyophilization.

The purified GTF is then applied to a gel filtration column capable of retaining materials of molecular weight 6000 or less. Suitable gel filtration materials include, but are not limited to, Biogel P-6 and Sephadex 25. The column is eluted with a suitable buffer. A preferred buffer is 0.1-100 mM ammonium acetate. A more preferred buffer is 50 mM ammonium acetate. The fractions containing biologically active material are collected and concentrated.

The purified GTF is then applied to a gel filtration column capable for retaining material of molecular weight 2000 or less. Suitable gel filtration materials include, but are not limited to, Biogel P-2 and Sephadex G15. The column is eluted with a suitable buffer. A preferred buffer is 0.1-100 mM ammonium acetate. A more preferred buffer is 50 mM ammonium acetate. The fractions are assayed for biological activity utilizing assays as previously described, and are combined and concentrated. A typical assay is described below. This partially purified GTF is suitable for use as a blood sugar reducing factor.

The GTF-containing fraction may be analyzed by reverse phase HPLC and eluted with a suitable solvent system. The fractions are assayed for biological activity by one of the previously described procedures.

Alternatively, the purified GTF from the last gel filtration column (molecular weight retention 2000 or less) may be further purified by one or more HPLC separations. A suitable HPLC column for the first HPLC separation include, but are not limited to a CMHPLC ion exchange column. A typical elution comprises a gradient increasing from 0.2 to 2.0 M ammonium acetate. The fractions may be monitored by one or more of the previously described procedures, or detected by U.V. spectrometry at 280 nm.

The biologically active fraction may then be further purified on a reverse phase HPLC column to give a substantially pure material which is characterized below. Suitable reverse phase HPLC columns for this second HPLC separation include, but are not limited to C18 HpLC columns. A preferred solvent systems includes a gradient elution increasing from water containing 0.1% TFA to 70% acetonitrile in water containing 0.1% TFA.

Thus, the invention further includes the substantially purified GTF fraction, obtained from the above described fractionation protocol. This material is believed to be a quinoline derivative. The invention includes the quinoline derivatives and their analogs. By analogs are meant quinoline isomers which are substituted by lower (C$_1$-C$_4$) alkyl, aryl, or heterocyclic moieties at the amine and alkoxy positions. The partially purified GTF fractions and the quinoline isomers and their analogs have the following characteristics: The ability to increase $^{14}$C-glucose uptake, glucose oxidation and lipid synthesis in adipocytes; the ability to reduce blood sugar, triglyceride and cholesterol levels when injected into an animal; and to increase carbon dioxide production when added to a yeast culture.

The purified quinoline derivative has a molecular weight of 174 and the following biochemical and biophysical characteristics:

1. It is a cationic compound, soluble in water but not in chloroform, retarded on a C18 reverse phase column and eluted with 40% acetonitrile in 0.1% trifluoroacetic acid.
2. It reacts with ninhydrin reagent. When applied to an amino acid analyzer without acid hydrolysis, it eluted as a peak immediately following ammonia. No known amino acid eluted at the same position. After acid hydrolysis, it eluted as a single peak at the glycine position.
3. It binds Chromium (III) as determined by mixing with a $^{51}Cr$ isotope and repeating chromatography on a C18 column.
4. The U.V. spectrum in acidic (0.1 N HCl) solution shows 3 major peaks at 301.5, 258.5, and 139.0 nm. In alkaline solution (0.1 NaOH), the peaks shifted correspondingly to 323.0, 263.0, and 214.5 nm.
5. From the fraction with the molecular mass 174, a fragment of Mr 144 is detected by mass spectrometry after electron ionization.
6. In an in vitro rat fat pad assay ($^{14}C$-glucose uptake and lipid synthesis) 5 ug of the active fraction was approximately equivalent in biological activity to 0.25 ng of insulin. In vivo assays (intraperitoneal injection of the fraction into mice) show that 50 ug of the fraction decreases blood glucose in one test from 147 to 71 mg/dl and in another from 109 to 80 mg/dl.
7. 'HNMR spectrum (500 mHz) was (ppm): 3.32 (s,3 H), 4.37 (s,2 H), 7.2 (m,2 H), 7.45 (m, 1 H), 8.01 (m, 1 H), 8.13 (s, 1 H).
8. From all the characteristics described above, the active component was determined to be a quinoline derivate with a structural formula selected from the group consisting of:

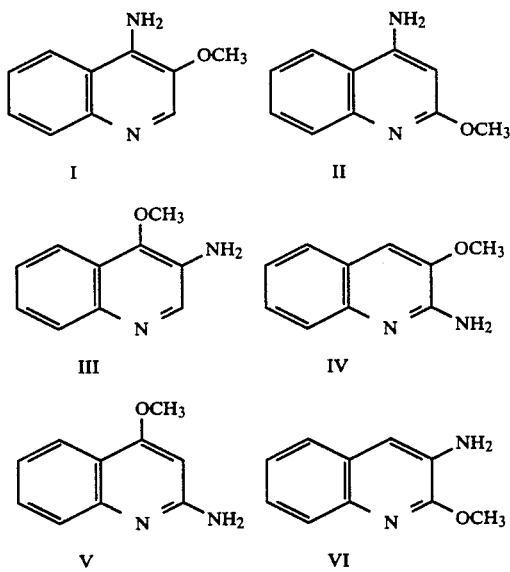

Quinoline derivative VI and an analog of derivatives VI and II were reported by Wojahn, *Arznceimittel-Forsch*, 2:163–165 (1952) as having some tuberculostatic activity.

The purified GTF fractions, quinoline derivatives and their analogs are useful in reducing blood sugar levels in animals. As will be understood by one of skill in the art, effective dose ranges of these materials will depend on the blood sugar reducing activity of the material used and on patient characteristics such as age and weight. Further, the effective dose will depend upon the route of administration. Acceptable routes of administration include, but are not limited to oral, subcutaneous, intramuscular, intravenous, and intraperitoneal injection. The material of this invention may be administered as part of a formulation containing suitable excipients and auxilliaries. These formulations may be prepared by any of the methods well-known in the pharmaceutical art, for example, as described in *Remington's Pharmaceutical Sciences* (16th edition, 1980).

EXAMPLE 1

For the purposes of this example, a commercially available autolyzed brewer's yeast extract, DIFCO YEAST EXTRACT was used. It is available from Difco Laboratories of Detroit, Mich. The DIFCO YEAST EXTRACT consists of the water soluble portion of autolyzed yeast. The Sephadex G-75 column material is from Pharmacia, N.J. Bio-gel P-2 and P-6 column materials are from Bio-Rad of Richmond, Calif.

Sephadex G-75 is a polysaccharide based gel-filtration medium with a 50000 molecular weight cut off. Bio-gel P-6 and P-2 are polyacrylamide based gel-filtration media with 5000 and 2000 molecular weight cut offs, respectively.

The CMHPLC column and the Altex C18 reverse phase HPLC column is available from the Beckman Instrument Company (Fullerton, Calif.).

Determination of Biological Activity of the Putative Glucose Tolerance Factor

The biological activities of the putative GTF isolated from the yeast extract were analyzed by the measurement of $^{14}C$-glucose uptake, glucose oxidation and lipid synthesis in rat adipocytes. Insulin was used as an internal standard. Rat epididymal fat pads, after removal from the rats (weight 25014 300 gm) were digested with collagenase (10 mg per gm of fat pad) in 10 ml of Krebs-Ringer buffer (118.0 mM NaCl, 5.0 mM KCl, 1.3 mM $CaCl_2$, 1.2 mM $KH_2PO_4$, 1.3 mM $MgSO_4$, 25.0 mM $NaHCO_3$ and 20 mM Hepes, pH 7.4) containing 2% bovine serum albumin (BSA) and 0.1 mg/ml of dextrose. The digestion was carried out in a 37° C. water bath shaker at 100 oscillations/minute for 20–30 minutes. The adipocytes were then filtered through a layer of nylon cloth and collected in a 15 ml centrifuge tube. The adipocytes were washed 5 times with the same digestion buffer and centrifuged in a clinical centrifuge (set at scale 2 for 1 minute) to remove the collagenase.

The adipocytes were then resuspended in the same buffer and the cell number adjusted to $2-2.5\times 10^5$ adipocytes in a 500 ul volume. Then, 100 ul of the adipocyte mixture was added to a 10×75 mm tube and combined with 300 ul of Krebs-Ringer buffer containing 2% BSA and 0.1 mg/ml dextrose, 50 ul of insulin (0 to 5.0 ng/ml in final concentration), and 50 ul of $^{14}C$-glucose (0.05uCi, 200 mCi/mM). The reaction mixture was gassed with 5% $CO_2$, capped and incubated in a water bath shaker at 37° C. and 80 oscillations/minute for 2 hours. The reaction was terminated by cooling the cells in tap water followed by immediate transfer of 250 ul of the cells from each reaction tube to a microfuge tube containing 150 ul of silicone oil The microfuge tubes were then centrifuged in a microfuge for 1 minute, then transferred to a liquid scintillation vial containing 5 ml of scintillation fluid. The $^{14}C$-glucose incorporation in to the adipocytes was measured by a Beckman liquid scintillation counter (Model 9800).

For $^{14}C$-glucose oxidation, the reaction was carried out in a 17×100 mm tube in the same manner as described for the $^{14}C$-glucose uptake test except that a 10×75 mm glass tube containing a 7×65 mm filter paper strip was placed inside the glass tube. After the reaction was complete, 0.2 ml of a 25% beta-phenylethylamine solution in methanol was injected with a syringe into the inner glass tube to wet the filter paper strips, and 0.4 ml of 4 N $H_2SO_4$ was injected directly into the reaction mixture. The reaction was continued for an additional 30 minutes to ensure that the $^{14}CO_2$ gas released from the adipocytes was absorbed by the filter paper strip. The absorbed $^{14}CO_2$ gas was measured in a liquid scintillation vial containing 5 ml of scintillation fluid.

For $^{14}C$-lipid synthesis, the reaction conditions were the same as that in the $^{14}C$-glucose uptake in adipocytes except that the $^{14}C$ lipids synthesized in the adipocytes were extracted with Dole's mixture (10 parts heptane, 40 parts isopropanol and 11 part 1 N $H_2SO_4$). After the reaction was complete (2 hours of incubation at 37° C.), the cells were separated by silicone oil in a microfuge tube as described above, and the adipocytes were transferred to a glass tube containing 0.8 ml of Dole's mixture. The tubes were then maintained at room temperature for 5 minutes. The mixture was vortexed, followed by the addition of 0.5 ml heptane and 0.5 ml $H_2O$ to each tube. After 5 minutes, the tubes were vortexed again, and one-half volume 325 ul) of the heptane layer transferred to a vial containing 5 ml of liquid scintillation fluid. The $^{14}C$-lipid extracted from the adipocytes was measured by a liquid scintillation counter.

Fractionation on Sephadex G-75 Column

One gram of DIFCO YEAST EXTRACT was dissolved in 5 ml of $H_2O$, and centrifuged at 3000 rpm in a clinical centrifuge for 5 mintues. The resulting supernatant was applied to a Sephadex G-75 column (1.5 cm×100 cm) and eluted with $H_2O$. Six pools of fractions (approximately 10-13 fractions per pool) were collected and lyophilized. The biological activity of each pooled fraction was measured in adipocytes as previously described.

Among the 6 pooled fractions, only pool I and pool II possessed biological activity as determined by $^{14}C$-glucose uptake and lipid synthesis in rat adipocytes. Pools I and II from the Sephadex G.75 column were combined and lyophilized. The yield of these two pools was about 60-90 ml from 1 gm of yeast extract or 3-30 mg of dry material.

Acid-Ethanol Extraction

Fractions with high biological activity obtained from the Sephadex G-75 column chromatography were further purified by an acid-ethanol extraction. Biologically active material (60-90 mg) was dissolved in 5 ml of water followed by the addition of 2.4 volumes of 95% ethanol. The solution was then acidified to a final concentration of 0.15 N HCl. The mixture was kept in ice water for 1 hour and then centrifuged at 3000 rpm (Beckman TJ6 centrifuge) at 4° C. for 10 minutes. After acid-ethanol extraction, the supernatant contained about 15% by weight of the starting biological material (the precipitate constituted 85% by weight). The supernatant of the acid-ethanol extraction had biological activity 1.5-2.0 times higher in adipocytes than that of Pools I and II from the G-75 column. The precipitate of the acid-ethanol extraction showed lower $^{14}C$-glucose uptake activity. The supernatant was lyophilized.

Separation on Biogel P-6 Column

The lyophilized powder from the acid-ethanol extraction was dissolved in 50 mM ammonium acetate and loaded onto a Biogel P-6 column which was 1.5 cm in diameter and 75 cm in height. The material was eluted with 50 mM ammonium acetate and 2 ml fractions were collected. Five peaks were observed and tested by the foregoing described method for bioactivity in adipocytes ($^{14}C$-glucose uptake, glucose oxidation and lipid synthesis). Peak No. 4 gave the highest bioactivity using the adipocyte assays. Peak No. 4 (20 ml) was lyophilized to give 0.05-0.5 mg of material per 1 gram of yeast extract.

Purification on Biogel P-2 Column

The dried powder from Peak No. 4 of the Biogel P-6 column was dissolved in 50 mM ammonium acetate and loaded into a column (1.5 cm in diameter and 75 cm in height) filled with Biogel P-2 material. The column was eluted with 50 mM ammonium acetate and 2 ml fractions were collected. Five peaks were observed. Each peak was pooled and tested for bioactivity by the previously described procedures. Peak No. 3 showed activity in adipocytes ($^{14}C$-glucose uptake, glucose oxidation and lipid synthesis) and the in vivo assay in mice as described below. Peak No. 3 was lyophilized to yield 0.01-0.1 mg dry material from the starting 1 g of yeast extract.

Analysis of Peak No. 3 Fraction

The Peak No. 3 dry fraction was dissolved in water, loaded onto a C-18 reverse phase HPLC column (0.46 cm in diameter and 15 cm in height) and eluted with a two buffer gradient system comprising 0.10% TFA and 70% acetonitrile containing 0.10% TFA. One ml fractions were collected and tested for bioactivity in adipocytes ($^{14}C$-glucose uptake, glucose oxidation and lipid synthesis). The most active fraction appeared in the first 5 minutes of elution. After standing in a refrigerator for more than 10 days at 4° C., more peaks appeared when the material was rechromatographed. This indicated that either this fraction was not pure or that some reaction has occurred on standing.

Mass spectrometry of the Peak No. 3 after probe desorption showed a major fraction with a molecular ion at 1471 and two minor fractions with molecular ions at 670 and 558.

The material of Peak No. 3 was ninhydrin positive, which indicates a possible peptide linkage.

Tests on Mice

The effect on mouse glucose levels from injections of either the previously described Peak No. 3 or saline are reported in Table 1.

TABLE NO. 1

EFFECT OF YEAST EXTRACT P2-3 FRACTION ON GLUCOSE LEVEL IN MICE

| Animal # | (Condition) | Date Tested | Serum Glucose (mg %) at | | | | | |
|---|---|---|---|---|---|---|---|---|
| | | | Min 0 | Min 15 | Min 30 | Min 60 | Min 90 | Min 120 |
| 1 | (overnight fasted) | 2-18-85 | 102 | 99 | 87 | 80 | — | 53 |
| 2 | (overnight fasted) | 4-26-85 | 80 | 110 | 87 | 67 | — | 52 |
| 3 | (overnight fasted) | 4-30-85 | 81 | 100 | — | 65 | — | 51 |
| 4 | (3 hr fasted) | 5-6-85 | 187 | 164 | 118 | 109 | — | — |
| 5[a] | (3 hr fasted) | 5-14-85 | 156 | 176 | — | 142 | 83 | 52 |
| 6 | (3 hr fasted) | 5-14-85 | 131 | — | — | 108 | 109 | 95 |
| 7 | (3 hr fasted) | 5-14-85 | 139 | 138 | — | 123 | 99 | 105 |
| 8 | (3 hr fasted) | 5-14-85 | 156 | 122 | — | 97 | 129 | 153 |
| 9 | (3 hr fasted) | 5-14-85 | 148 | 161 | — | 132 | 128 | 108 |
| Control 5[b] | (3 hr fasted) | 5-15-85 | 161 | — | 178 | 194 | — | 160 |
| Control 6[b] | (3 hr fasted) | 5-15-85 | 124 | — | 148 | 138 | — | 113 |
| Control 7[b] | (3 hr fasted) | 5-15-85 | 142 | — | 155 | 145 | — | 135 |
| Control 8[b] | (3 hr fasted) | 5-15-85 | 183 | — | 188 | 206 | — | 207 |

[a]Animal #5 was tested by P2-3-HPLC fraction (that is P2-3 fraction further purified by HPLC).
[b]Control 5-6-7-8 were the same animals used for the GTF test but injected with saline.

All of the animals tested were injected with 0.2 ml of a 0.1% solution of Peak No. 3 material in water or with 0.2 ml of a 0.9% saline solution for the control. Animals #5–8 were utilized for both the control and the actual tests. All of the animals showed a reduction in blood sugar after injection with Peak No. 3 material. Particularly interesting is the comparison of animals #5–8 which were given a saline injection on one day and an injection of biologically active fraction on another. No decrease in blood sugar after the saline injection was noted. However, after the injection of the biologically active fraction, there was a definite decrease in blood sugar in three animals and a temporary drop in the fourth. There was a clear-cut decrease in blood sugar in animals #1–4 and in animal #9. The sharpest drop in blood sugar was seen in animal #5 after the injection of the purest fraction

EXAMPLE 2

Isolation of a quinoline derivative from Biogel P-2 peak No. 3 fraction

The Biogel P-2 peak No. 3 fraction was applied to a CMHPLC ion-exchange column (7.5×75 mm) and eluted with a gradient which increased from 0.2 to 2.0 M ammonium acetate A total of 9 peaks were detected by U.V. spectrometry at 280 nm. Peak No. 8, which had a retention time of approximately 29 minutes, had the greatest biological activity using the adipocyte assay ($^{14}$C-glucose uptake, glucose oxidation and lipid synthesis) as described above.

CMHPLC peak No. 8 was further purified by gradient elution from an Altex C18 HPLC column (with the solvent changing from 0.1% trifluoroacetic acid to 70% acetonitrile containing 0.1% trifluoroacetic acid) to give a quinoline derivative with molecular weight 174 and the following biochemical and biophysical characteristics:

1. It was a cationic compound, soluble in water but not in chloroform, retarded on a C18 reverse phase column and eluted with 40% acetonitrile in 0.1% trifluoroacetic acid.
2. It reacted with ninhydrin reagent. When applied to an amino acid analyzer without acid hydrolysis, it eluted as a peak immediately following ammonia. No known amino acid eluted at the same position. After acid hydrolysis, it eluted as a single peak at the glycine position.
3. It bound Chromium (III) as determined by mixing with a $^{51}$Cr isotope and repeating chromatography on a C18 column.
4. The U.V. spectrum in acidic (0.1 N HCl) solution showed 3 major peaks at 301.5, 258.5, and 139.0 nm. In alkaline solution (0.1 NaOH), the peaks shifted correspondingly to 323.0, 263.0, and 214.5 nm.
5. From the fraction with the molecular mass 174, a fragment of Mr 144 was detected by mass spectrometry after electron ionization.
6. In an in vitro rat fat pad assay ($^{14}$C-glucose uptake and lipid synthesis) 5 ug of the fraction with mass 174 was found to be equivalent in biological activity to 0.25 ng of insulin. In vivo assays (intraperitoneal injection of the fraction into mice) showed that 50 ug of the fraction decreased blood glucose in one test from 147 to 71 mg/dl and in another from 109 to 80 mg/dl.
7. The 'NMR spectrum (500 MHz) was (ppm): 3.32 (s,3 H), 4.37 (s,2 H), 7.21 (m,2 H), 7.45 (m, 1 H), 8.01 (m, 1 H), 8.13 (s, 1 H).
8. From all the characteristics described above and from the NMR spectrum the purified component was determined to be a quinoline derivate with a structural formula selected from the group consisting of:

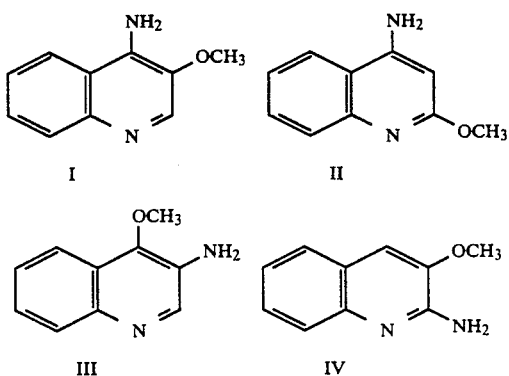

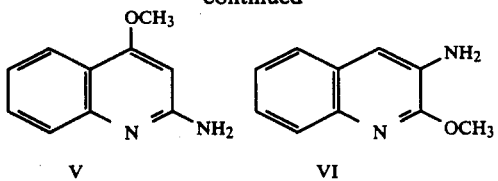

While the invention has been described in connection with certain preferred embodiments, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A method for reducing serum glucose levels in an animal, comprising administering an effective amount of a glucose tolerance factor to an animal in need of reduced serum glucose, wherein said glucose tolerance factor has a structural formula selected from the group consisting of:

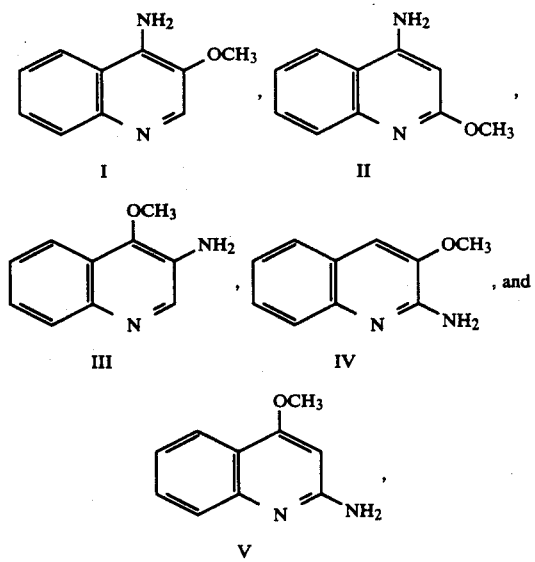

2. A method for reducing serum glucose levels in an animal, comprising administering an effective amount of a substantially purified glucose tolerance factor to an animal in need of reduced serum glucose obtained by a process comprising the steps, in order, of:
   (a) passing an aqueous extract of brewer's yeast through a Sephadex G-75 column,
   (b) collecting the fractions which exhibit glucose tolerance factor activity,
   (c) extracting the solids in the collected fractions with an acid-ethanol mixture,
   (d) passing the solids from the acid-ethanol extraction in an ammonium acetate solution through a column containing Biogel P-6 therein,
   (e) collecting the fractions containing glucose tolerance activity,
   (f) separating the fractions containing glucose tolerance activity collected in step (e) in an ammonium acetate solution with a Biogel P-2 column,
   (g) collecting the fractions with glucose tolerance activity,
   (h) passing the fractions having glucose tolerance activity obtained in step (g) through a CMHPLC ion-exchange column using an ammonium acetate gradient,
   (i) collecting the fractions with glucose tolerance activity,
   (j) passing the fractions collected in step (i) having glucose tolerance activity through a C-18 reverse phase HPLC column using a trifluoroacetic acid in water-acetonitrile gradient, and
   (k) collecting the fractions with glucose tolerance activity; to give a substantially purified glucose tolerance factor.

3. A method for reducing serum glucose levels in an animal, comprising administering an effective amount of a substantially purified glucose tolerance factor to an animal in need of reduced serum glucose obtained by a process comprising the steps of:
   (a) passing an aqueous extract of brewer's yeast through a Sephadex G-75 column,
   (b) collecting the fractions which exhibit glucose tolerance factor activity,
   (c) extracting the solids in the collected fractions with an acid-ethanol mixture,
   (d) passing the solids from the acid-ethanol extraction in an ammonium acetate solution through a column containing Biogel P-6 therein,
   (e) collecting the fractions containing glucose tolerance activity,
   (f) separating the fractions containing glucose tolerance activity collected in step (e) in an ammonium acetate solution with a Biogel P-2 column,
   (g) collecting the fractions with glucose tolerance activity,
   (h) passing the fractions having glucose tolerance activity obtained in step (g) through a CMHPLC ion-exchange column using an ammonium acetate gradient,
   (i) collecting the fractions with glucose tolerance activity,
   (j) passing the fractions collected in step (i) having glucose tolerance activity through a C-18 reverse phase HPLC column using a trifluoroacetic acid in water-acetonitrile gradient, and
   (k) collecting the fractions with glucose tolerance activity, to give a substantially purified glucose tolerance factor; wherein said substantially purified glucose tolerance factor has the following characteristics:

it decreases blood sugar in mammals;
   it increases $^{14}C$-glucose uptake and lipid synthesis in rat adipocytes;
   it is ninhydrin positive;
   it is a cationic compound which is soluble in water and insoluble in chloroform;
   it is retarded on a C-18 reverse phase column eluted with 40% acetonitrile containing 1% trifluoroacetic acid;
   it binds chromium (III);
   it has a U.V. spectrum with three major peaks at 301.5, 358.5 and 139.0 nm in acetic solution (0.1 NHCl);
   it has a shifted U.V. spectrum with three major peaks at 323.0, 363.0 and 214.5 nm in alkaline solution (0.1 N NaOH);
   it has a mass spectrum with a molecular mass 174 and a daughter ion at 144 as measured by mass spectrometry after electron ionization; and
   it has a $^1H$ NMR spectrum (ppm) of: 3.32 (s,2 H), 4.37 (s,2 H), 7.21 (m,1 H), 8.01 (m, 1 H) and 8.13 (s,1 H).

* * * * *